United States Patent [19]

Hrvoic et al.

[11] 3,966,409
[45] June 29, 1976

[54] NUCLEAR MAGNETOMETERS FOR EARTH'S FIELD MEASUREMENTS BASED ON DYNAMIC POLARIZATION OF NUCLEI AND FREE RADICAL SUBSTANCE FOR USE THEREIN

[76] Inventors: Ivan Hrvoic, 2825 Islington Ave., N., Weston, Ontario, Canada; Kresimir Humski, Adamiceva 3, 41020 Zagreb, Yugoslavia

[22] Filed: Sept. 9, 1974

[21] Appl. No.: 504,719

[30] Foreign Application Priority Data
Nov. 30, 1973 Canada.................................. 187093

[52] U.S. Cl........................ 23/230 R; 260/307 FA
[51] Int. Cl.² ................ C07D 263/00; G01N 27/26
[58] Field of Search............. 23/230 R; 260/307 FA

[56] References Cited
UNITED STATES PATENTS 3,489,522  1/1970  McConnell.......................... 23/230 B
3,668,214  6/1972  McConnell et al................. 23/230 B

OTHER PUBLICATIONS

Hackh's Chemical Dictionary, 4th ed., McGraw-Hill, p. 426, 1969.

*Primary Examiner*—Robert M. Reese
*Attorney, Agent, or Firm*—James R. Hughes

[57] ABSTRACT

A free radical substance for use in a suitable solvent as the sample material in nuclear dynamic polarization type magnetometers which is a free radical substance of the oxazolidine group wherein the radicals $R_1$ and $R_2$ are chain radicals of the type $-(CH_2)_nCH_3$, wherein n varies from 0 to 2. It has been found that the free radical 2,2,4,4, tetramethyl oxazolidine-3-oxyl has outstanding characteristics for this purpose.

4 Claims, 6 Drawing Figures

NUCLEAR MAGNETOMETERS FOR EARTH'S FIELD MEASUREMENTS BASED ON DYNAMIC POLARIZATION OF NUCLEI AND FREE RADICAL SUBSTANCE FOR USE THEREIN

This invention relates to nuclear magnetometers for measuring weak magnetic fields particularly the earth's magnetic field based on dynamic polarization of nuclei and to a free radical substance for use therein.

The theory of nuclear magnetic resonance and dynamic polarization (Overhauser-Abragam effect) are well known and are well described in the literature. See for example: A. Abragam, Principles of Nuclear Magnetism, Oxford University Press, 1961. Because of this only a short resume giving only basic facts necessary for understanding the operation of this type of magnetometer is given.

Nuclear magnetic resonance magnetometers make use of the proportionality between frequency of resonance ($\omega_o$) and magnetic field strength (H):

$$\omega_o = \gamma H$$

where $\gamma$ is the gyromagnetic ratio, a constant for a specific nucleus or electron. Protons have a high nuclear gyromagnetic ratio ($\gamma_p/2\pi = 4.25760$ kHz/G) and fluorine follows ($\gamma_f/2\pi = 4.0055$ kHz/G). Electrons have a much higher gyromagnetic ratio ($\gamma_e/2\pi = 2.80246$ MHz/G for a free electron).

Because of the wide choice of samples, the narrow spectral lines and the highest gyromagnetic ratio among nuclei, protons are the favorite nuclei for nuclear magnetic resonance (NMR) magnetometers. As the strength of the NMR signal varies approximately with the square of measured magnetic field, in low fields the NMR signals are too small to be used for high resolution magnetometry. Two ways of overcoming this difficulty are in use in weak field magnetometry. The first is polarization by applying a strong DC magnetic field to the sample at right angles to the measured field direction and subsequent measurement of the frequency of precession of nuclei. This is the system used in proton precession magnetometers.

The second method is the use of dynamic polarization or the Overhauser-Abragam effect where permanent or dynamic polarization of nuclei is achieved by adding to the sample of say protons, an assembly of unpaired electrons which then couple with protons magnetically and saturating an electron resonance line by applying a strong RF magnetic field at the frequency $\omega_e = \gamma_e H$ and at right angles to the field H. Polarization of protons is proportional to the ratio of two resonant frequencies $\omega_e/\omega_p$. To achieve as high dynamic polarization as possible, unpaired electrons are attached to molecules where they experience a strong local field of some nuclei, as for example, the use of nitroxide free radicals as the sample material in the magnetometer. In this case the unpaired electron dwells close to the nitrogen nucleus (which has a spin I = 1) and experiences a local field of as much as 14–17 Gauss. The unpaired electrons will have resonant spectral lines different from zero even in zero applied magnetic field and in weak fields such as the earth's field, the ratio $\omega_e/\omega_p$ can be as high as 70,000 for nitroxide free radicals. However due to other factors, the ultimate achievable dynamic polarization is in the order of 5,000.

There is a limited choice of chemically stable free radical substances having high zero-field splitting that may be used in nuclear magnetometers based on dynamic polarization. Canadian Pat. No. 764,597 issued to H. Lemaire et al on Aug. 1, 1967 discloses a number of stable free radicals of the nitroxide group. The zero field splitting ($a_H = 14-17G$) is caused by interaction of a free electron and a nucleus of nitrogen which has a spin $I = 1$. In a strong magnetic field the EPR (electron paramagnetic resonance) spectrum consists of three equally spaced spectral lines separated by 14–17G. In a low field ($H_e$), the EPR spectrum degenerates to two EPR lines which appear at the RF frequency corresponding to 3/2 $a_H$ (21–25G) and are mutually separated by 4/3 $H_e$. As saturation of each of the two EPR lines gives almost equal and opposite amplification of the NMR signal, it is of utmost importance that the EPR lines be as narrow as possible to avoid overlapping and consequently a reduction of amplification. The EPR line width depends largely on the structure of the free radical used and the thermodynamic properties of the solvents used. Solvents of low viscosity have generally less influence on EPR line broadening.

Although the free radicals disclosed in Canadian Pat. No: 764,597 chief of which is known as "TANO" have good characteristics for this purpose, it has been found that the stability of some of these free radicals has not been adequate especially in the presence of oxygen and when in a concentrated state.

It is an object of the present invention to provide a free radical substance for use in nuclear dynamic polarization magnetometers that has very good nuclear and electro-magnetic properties and which also has excellent stability at high concentration over wide temperature ranges, and for extended periods of time.

This and other objects of the invention are achieved by a free radical substance of the oxazolidine group (FIG. 5) where $R_1 = R_2 = CH_3$ giving rhe radical (2, 2, 4, 4, tetramethyl oxazolidine-3-oxyl) herein designated as "TEMOO" (Tetramethyl oxazolidine oxyl).

In drawings which illustrate embodiments of the invention,

Having the nuclear magnetization of the sample greatly increased by applying a strong RF magnetic field at the electron resonance frequency at right angles to the magnetic field direction, any conventional method of detection of the NMR signal and the measurement of its frequency can be used down to magnetic fields of a fraction of a gauss. To make a pulsed device for measurements of magnetic field strength (nuclear induction magnetometer) it is only necessary to deflect the vector of nuclear polarization into the plane perpendicular to the magnetic field. Subsequent precession of the magnetization vector will induce an electric signal in a coil wound around the sample and orientated at approximately right angles to the magnetic field direction. Continuous measurement of magnetic field can be achieved by applying a small excitation field at a frequency close to the NMR precession frequency in a plane perpendicular to the NMR precession frequency in a plane perpendicular to the magnetic field direction. The excitation field deflects the magnetization vector from the magnetic field direction and causes it to precess around its direction inducing an AC signal in a coil wound around the sample. The frequency of this signal is proportional to the field strength.

Figure 1:
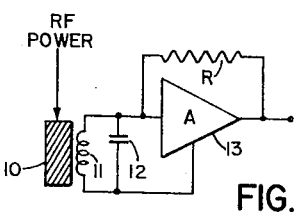
FIGS. 1 to 4 are nuclear dynamic polarization magnetometer detector systems.

Fig. 1 shows a simple circuit which is in effect a maser oscillator operating on the above principle The sample, e.g. TEMOO in an appropriate solvent is contained in a suitable container 10. An RF magnetic field is applied as shown. A coil 11 is wrapped around the sample and with capacitor 12 forms the resonant circuit for feedback amplifier 13. The NMR signal is amplified and fed back to the coil thus providing self-excitation and oscillation at the NMR frequency.

Figure 2:
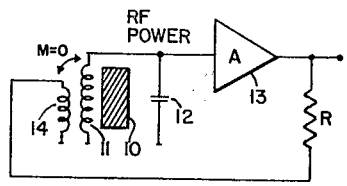
Figure 3:
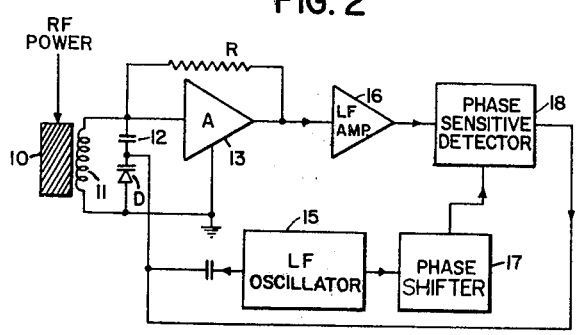

FIG. 2 shows a circuit (spin generator) similar to FIG. 1 but with the NMR signal amplified and fed back to a separate coil 14 decoupled from the pick-up coil 11 and providing self-excitation and oscillations at the NMR frequency. FIG. 3 is a marginal oscillator circuit wherein the amplifier 13 has a positive feedback and oscillates independent of NMR signal. The frequency of oscillations is modulated to cross the NMR line by low frequency oscillator 15 and AC correction signal is obtained from the marginal oscillators. By low frequency amplifier 16, phase shifter 17, and phase sensitive detector 18, this signal is amplified and rectified and is used to control the frequency of the oscillator 13, via voltage variable capacitor D.

Figure 4:
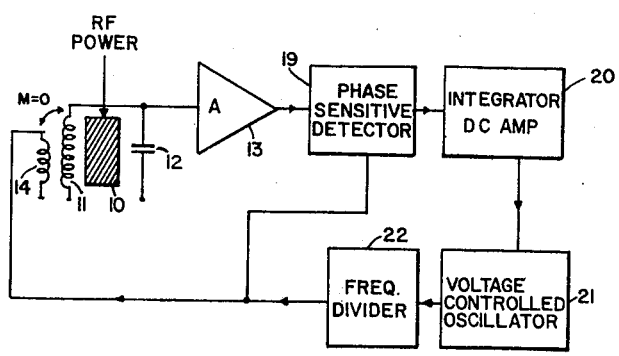

FIG. 4 shows a circuit where the excitation is obtained from a separate source. The signal picked up in pick-up coil 11 is of the dispersion type and is suitable after being applied to phase sensitive detector 19 and integrator and DC amplifier 20 to control the frequency of the excitation oscillator 19 (with frequency divider 22) connected to excitation coil 14. For more detailed discussion of dispersion type nuclear magnetic resonance magnetometers reference should be made to Canadian Pat. No. 932,801 issued Aug. 29, 1973 to the present applicant.

Figure 5:
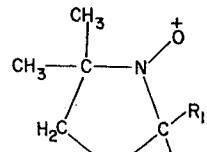
FIG. 5 is the chemical formula for the oxazolidine group of free radicals.
Figure 6:
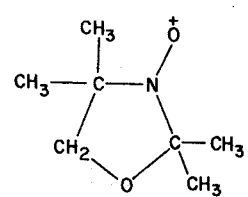
FIG. 6 is the chemical formula of the free radical TEMOO.

FIG. 5 shows the generalized chemical formula of the oxazolidine group of free radicals. It has been discovered that the EPR line width decreases as $R_1$ and $R_2$ become lighter and when $R_1 = R_2 = CH_3$, the radical (2, 2, 4, 4, tetramethyl oxazolidine-3-oxyl, TEMOO) shows perfect stability even in impure and concentrated state at warm temperatures, its genuine EPR line width being only 0.45G. This radical has the formula as shown in FIG. 6. Tests have shown that when dissolved in the solvent, deoxygenated methyl alcohol, the free radical TEMOO has the same narrow EPR lines down to −80°C which is lower than any expected environmental temperature where a magnetometer would be used. In the same solution the radical can be heated to 65°C for several hours with no reduction of its concentration. This radical in concentrated impure state was left during several warm summer months exposed to air and showed no sign of decomposition. It appears to be very suitable for use in magnetometers which when used are exposed to harsh environmental changes of temperature, because of excellent stability, solubility in organic solvents, high mobility and narrow EPR lines, and easy and cheap production.

For dynamic polarization type magnetometers and similar devices, the overall characteristics of the radical TEMOO appear to surpass other presently known free radicals. The EPR characteristics of TEMOO are (a) zero field splitting constant $a_H = 15.75$ G in methanol and (b) line width of 0.45 G in diluted deoxygenated solutions. The optimum RF frequency for saturation of the upper EPR line in a solution of methanol has been found to be $\omega_{RF}/2\pi = 65.1$ MHz. The excellent stability of TEMOO makes the removal of molecular oxygen from solvents (necessary to avoid broadening of the EPR lines by paramagnetic molecular oxygen) very simple and easy. In contrast to the tedious and well known freeze-pump-thaw technique which is necessary for the insufficiently stable nitroxides used up to the present solutions of TEMOO in methyl hydrate can be boiled for 10–15 minutes and then sealed in containers afterwards giving very efficient deoxygeration. This makes the industrial production of magnetometer and other NMR device sensors simple and cheap. The evaporated methyl hydrate can be easily recaptured and reused and there is negligible evaporation of TEMOO during boiling.

The preparation of 2, 2, 4,4 tetramethyl oxazolidine-3-oxyl (TEMOO) is done in two steps (1) Synthesis of 2,2,4,4 tetramethyl oxazolidine and (2) oxidation of this into 2,2,4,4 tetramethyl oxazolidine-3-oxyl. These two steps may be carried out as follows:

The mixture of 20 g (0.225 mole) of 2-amino-2-methylpropan-1-ol, 32 g (0.552 mole) of acetone and 80 ml of dry benzene was placed into 250 ml round bottom flask equipped with a Dean-Stark trap for azeotropic distillation to which an efficient double-jacket condenser was attached. After 112 hrs. of reflux, 4.5 g of water was collected and the solvent was removed by distillation over a 30 cm Vigreaux column. The remaining product was distilled over the same column at 126°–128°yielding 21.1 g (73%) of clear liquid oxazolidine. The product was 97% pure according to glpc analysis (5 ft. column with 10% Carbowax 20M on Chromosorb W 60/80 at 100°). Impurities were benzene (2%), acetone (0.3%), and unreacted aminol (0.7%). In the nmr spectrum there are two signals at $\tau$ 8.9 (6H) and $\tau$ 8.8 (6H) from two pairs of methyl groups and a singlet at $\tau$4.6 (2H) for the $CH_2$ group. Analysis of the carbon and hydrogen contents are within the limits of 0.3%.

m-Chlorperbenzoic acid (4.23 g, 70% pure, 0.017 mole) in 35 ml of anhydrous ether was introduced dropwise during 30 minutes into an externally cooled (ice-salt mixture) 250 ml round bottom flask containing 2.00 g (0.015 mole) of 2,2,4,4-tetramethyloxazolidine in 35 ml of ether. The mixture was vigorously stirred during the addition. After the addition the flask was closed with a calcium chloride tube and stirred overnight at room temperature. The resulting orange-yellow mixture was washed thoroughly with 5% sodium bicarbonate solution and dried with magnesium sulfate overnight. Ether was removed by distillation over a Vigreaux column and the remaining nitroxide was distilled at 69° (130 mm) giving 1,21 g of product (54%). The product was 92% pure according to glpc analysis (5 ft column with 10% Carbowax 20 M on Chromosorb W 60/80 at 100° and injector temperature at 100° because of possible decomposition) with ether as impurity. In the ir spectrum there is characteristic band of the N → O group at 970 $cm^{-1}$.

The above description is chiefly concerned with the free radical TEMOO, however certain compounds of the oxazolidine group (refer to FIG. 5) may be used although they do not give such good results. It has been found that compounds of this group where $R_1$ and $R_2$ are chain radicals of the type — $(CH_2)_n CH_3$ and $n$ varies from 0 to 2 will give useful results.

We claim:
1. A method of measuring weak magnetic fields comprising:
   a. placing in the magnetic field to be measured, a sample of a chemical substance made up of an assembly of nuclei with magnetic moments different from zero, the transition energy between the two adjacent energy states of nuclear magnetic moments being strictly proportional to the applied magnetic field and an assembly of unpaired electrons with unpaired spin and magnetic moments, said nuclear and electron magnetic moments being coupled by dipolar or scalar coupling or both, the said unpaired electrons in the sample being provided by a free radical chemical substance of the oxazolidine group

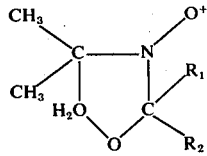

wherein the radicals $R_1$ and $R_2$ are chain radicals of the type $—(CH_2)_n CH_3$, where n varies from 0 to 2,
   b. saturating with a strong RF magnetic field of frequency close to the electron energy transition, the said electron transitions producing a strong dynamic polarization of nuclear magnetic moments, and
   c. detecting and measuring by electrical means the transition energy states of nuclear moments.

2. A method of measuring weak magnetic fields as in claim 1 wherein the said unpaired electrons in the sample are provided by a free radical chemical substance of the oxazolidine group where $R_1 = R_2 = CH_3$ giving the radical (2,2,4,4, tetramethyl oxazolidine-3-oxyl).

3. A method of measuring weak magnetic fields as in claim 1 wherein the said nuclei are protons in an organic solvent rich in hydrogen.

4. A method of measuring weak magnetic fields as in claim 3 wherein the organic solvent is methyl hydrate.

* * * * *